United States Patent [19]

Milburn et al.

[11] Patent Number: 4,959,303

[45] Date of Patent: Sep. 25, 1990

[54] ASSAY FOR ANTIGENS BY BINDING IMMUNE COMPLEXES TO SOLID SUPPORTS FREE OF PROTEIN AND NON-IONIC BINDERS

[75] Inventors: Gary L. Milburn, Sunnyvale; Judith Rabbie, Palo Alto; Thomas M. Houts, Mountain View, all of Calif.

[73] Assignee: Syntex (U.S.A.) Inc., Palo Alto, Calif.

[21] Appl. No.: 135,869

[22] Filed: Dec. 21, 1987

[51] Int. Cl.$^5$ ............... G01N 33/53; G01N 33/536; G01N 33/537; C12Q 1/02

[52] U.S. Cl. ..................... 435/7; 435/29; 435/871; 436/510; 436/511; 436/518; 436/531; 436/538; 436/539; 436/540; 436/541; 436/543; 436/824; 436/828

[58] Field of Search ............... 435/7, 29, 871; 436/540, 824, 518, 538, 539, 541, 821, 828, 531, 178, 543, 510, 511

[56] References Cited

U.S. PATENT DOCUMENTS

| | | | |
|---|---|---|---|
| 4,254,082 | 3/1981 | Schick et al. | 422/55 |
| 4,255,412 | 3/1981 | Albert | 424/1 |
| 4,283,383 | 8/1981 | Masson et al. | 436/509 X |
| 4,427,782 | 1/1984 | Caldwell et al. | 436/542 |
| 4,450,231 | 5/1984 | Ozkan | 435/7 |
| 4,503,143 | 3/1985 | Gerber et al. | 435/7 |
| 4,666,863 | 5/1987 | Edwards et al. | 436/514 |
| 4,757,024 | 7/1988 | Roper | 436/507 |

FOREIGN PATENT DOCUMENTS

| | | | |
|---|---|---|---|
| 0059624 | 8/1982 | European Pat. Off. | 435/7 |
| 0217403 | 8/1987 | European Pat. Off. | 436/518 |
| 0269876 | 8/1988 | European Pat. Off. | 422/58 |

*Primary Examiner*—Jack Spiegel
*Attorney, Agent, or Firm*—Theodore J. Leitereg

[57] ABSTRACT

Methods are disclosed for detecting an antigen in a biological sample. The methods involve providing in combination a solid support, which is substantially free of specific binding proteins, and a medium comprising an antigen from the sample and an antibody for the antigen. The combination is incubated under conditions sufficient for the antibody when bound to the antigen to bind to the support. The presence or amount of antibody on the support or in the medium is determined and is related to the presence of antigen in the sample. The methods have particular application to the detection of gram-negative bacteria.

79 Claims, No Drawings

ASSAY FOR ANTIGENS BY BINDING IMMUNE COMPLEXES TO SOLID SUPPORTS FREE OF PROTEIN AND NON-IONIC BINDERS

BACKGROUND OF THE INVENTION

1. Field of Invention

This invention relates to a method for detecting an antigen in a biological sample suspected of containing the antigen. The invention has particular application to detecting gram-negative bacteria in a clinical specimen.

Numerous techniques are known for detecting antigens in a sample, such as a biological fluid, i.e., blood, urine, cell cultures. It is important to be able to quickly and accurately detect the presence of antigens such as gram-negative bacteria, i.e., *Chlamydia trachomatis*, *Chlamydia psittaci* and *Neisseria gonorrhoeae* because of the prevalence of diseases associated with such bacteria. Many of the techniques utilized to detect antigens involve cell culture procedures. Such procedures are relatively long and complicated and the results are greatly dependent on the skill of the technician. Many other techniques, for example electrophoresis, require complicated and/or costly instruments that are not readily available.

Many of the detection techniques involve immunoassays. Some of these techniques involve detecting antibodies to the antigen of interest. Such indirect techniques tend to be inaccurate because antibodies often remain in the human body after the disease has been cured. Therefore, it is preferable to assay for antigens rather than antibodies. Immunoassay techniques for the detection of antigens often involve enzyme immunoassays such the enzyme linked immunosorbent assay generally referred to as ELISA. Such assays typically involve detecting the antigen of interest by coating the antigen on a bare solid surface or a surface that has been pre-coated with a protein such as an antibody. After coating the surface of the support with the antigen, the surface is washed to remove unbound antigen. Thereafter, the antigen on the surface is contacted with antibody for the antigen that is labeled or is capable of being labeled. The surface is again washed and the antibody that has bound to the surface of the support is detected by detecting the label.

The number of washing steps required in the above procedure adds significant time and manipulation to the assay. There is, therefore, a need for a method for detecting antigens, especially antigens from gram-negative bacteria, that is more rapid, reliable and cost effective than tests now known or available. It is likewise important that such a test require less manipulation than presently available tests.

2. Description of Related Art

A method for determining *Chlamydia trachomatis* antigen in a clinical specimen is disclosed in U.S. Pat. No. 4,497,899. The method disclosed involves lysing Chlamydia cells in the specimen to release the antigen; coating a bare solid support with the cell lysate; separating the coated support from the specimen; treating the separated support with antibody to form an antigen-chlamydia antibody complex on the support; separating the complex from unbound antibody; treating the bound complex with labeled antiglobulin to form an antigen-antibody-labeled antiglobulin complex on the support; separating the latter complex from unbound labeled antiglobulin; and determining bound labeled antiglobulin as a measure of antigen in the specimen. U.S. Pat. No. 4,497,900 discloses a method for determining *Neisseria gonorrhoeae* analogous to that in U.S. Pat. No. 4,497,899.

An indirect method for determining an antigen in a liquid sample is disclosed in U.S. Pat. No. 4,067,959 involving adsorbing antigen of the same immunological type as the sample antigen onto a solid support surface, reacting a known quantity of specific labeled antibody in solution with the sample antigen and with the adsorbed antigen. The labeled antibody is in excess so that a portion of the labeled antibody is bound in the solution to the sample antigen and excess labeled antibody immunologically reacts with the adsorbed antigen on the surface. The surface is washed and then the quantity of reacted labeled antibody on the surface is determined as a measure of the antigen in the sample.

A method for assaying for the presence of a Chlamydial infection involving generating antibodies against the principal outer membrane protein of *Chlamydia trachomatis* is disclosed in U.S. Pat. No. 4,427,782. The method comprises treating a sample suspected of containing chlamydial infection to solubilize the Chlamydia outer cell membrane protein, contacting the generated antibodies with the solubilized specimen and determining the reaction between the antibodies and the solubilized specimen. European Patent Application 0,174,106 discloses a method of detection of cell membrane protein, especially principal outer membrane of *Chlamydia trachomatis*. Great Britain Patent Application Ser. No. 2 047 889A discloses serological testing for *Chlamydia trachomatis* antibodies by microimmunofluorescence of utilizing a formaldehyde stabilized antigen.

U.S. Pat. Nos. 4,145,406 and 4,254,082 disclose a method for determining a specific binding substance in a liquid sample employing a nonspecific adsorbent and a labeled form of a specific binding partner to the substance to be determined. U.S. Pat. No. 4,188,371 discloses a method employing immunoradiometric assay techniques for detecting Neisseria bacteria in a sample. The method involves lysing bacteria in the sample to be tested; contacting the lysate with radiolabeled antisera; incubating the resultant mixture and then contacting the mixture with a solid phase antigen or an antigen immunoadsorbent; incubating the resultant mixture and then monitoring the radioactivity of the supernatant.

SUMMARY OF THE INVENTION

The method of the present invention is directed to the detection of an antigen in a biological sample suspected of containing the antigen. The method involves providing in combination a solid support, which is substantially free of specific binding proteins and usually free of any specific binding substance, and a medium containing an antigen from the sample and an antibody for the antigen. The combination is incubated under conditions sufficient for the antibody when bound to the antigen to bind to the support. The presence or amount of antibody on the support or in the medium is determined and is related to the presence or amount of antigen in the sample.

The method of the present invention has particular application in the assay of gram-negative bacteria. Of special interest are assays for *Chlamydia trachomatis*, *Chlamydia psittaci*, *Neisseria gonorrhoeae* and *Treponema pallidium*.

DESCRIPTION OF SPECIFIC EMBODIMENTS

The present invention relates to a method for the detection of an antigen in a biological sample. The method involves providing in combination a solid support, which is substantially free of specific binding proteins, and a medium comprising antigen from the sample and an antibody for the antigen.

In the method of the present invention, the sample suspected of containing the antigen can be combined in an aqueous medium with an antibody for the antigen and the medium combined with the support. Alternatively, the support and the antibody can first be combined and then the sample added. In another alternative, the sample can be pretreated to extract antigen therefrom and the antigen can be combined as indicated above.

The combination is then incubated under conditions sufficient for the antibody when bound to the antigen to bind to the support. Thereafter, the amount of antibody on the support or in the medium is determined and is related to the presence or amount of antigen in the sample. The amount of antibody may be determined in a variety of ways, including, for example, separating the support from the medium and contacting the separated support with a detection medium including a labeled receptor for the antibody for the antigen and examining the support or the medium for the presence of the label.

The present method has wide application in the field of detection of antigens in biological samples. The invention provides a method that is more convenient than bacteria cultures or standard immunochemical methods. The present method provides a detection method that is more rapid and requires less manipulation than prior methods which provide for a sample suspected of containing an antigen to react with a support (either bare or pre-coated with a capture antibody), and removal of the unbound antigen, addition of an antibody to the bound antigen to form an immune complex between the antigen on the support and the antibody, and detection of the immune complex. The present invention provides an unexpected economy of reagents in that it requires only a small fraction of the amount of antibody to the antigen as is required in prior methods.

Before proceeding any further with a description of the specific embodiments of the present invention, a number of terms will be defined.

"Antigen"—the compound or composition to be detected, the material of interest. The antigen can be monoepitopic or polyepitopic. The antigen is capable of binding specifically to an antibody and will normally be soluble or can be caused to be soluble in the assay medium.

The antigens will normally be poly(amino acids), i.e., polypeptides and proteins, polysaccharides, lipopolysaccharides, glycoproteins, lipoproteins, ribonuclear proteins, and the like. The antigens will frequently be components of bacteria, viruses, mitochondria, nuclei, cell membranes and the like.

Bacteria include gram-negative bacteria, including but not limited to, Chlamydia trachomatis, Chlamydia psittachi, E. coli, Pseudonoms fluorescens, Azotobacter vinelandii, Proteus vulgaris, Hydrogenomanas sp., Aerobacter aerogenes, Nisseria gonorrhoeae, Treponema pallidum, Serratia marcescens, Achromobacter fischer, Bacillus subtilis, Bacillus megaterium, Sarcina lutea, Micrococcus pyogenes, Lactobacillus casei, Torulopsis utilis and Streptomyces griseus, Shigella, Campylobacter, Salmonella, Legionella, Hemophillus influenza, and so forth.

Polysaccharides are a combination of at least about three or four monosaccharides, linked together by glycosidic bonds. Polysaccharides include, for example, starch glycogen, cellulose and dextran.

Lipopolysaccharides (LPS) are molecules containing lipid and polysaccharide moieties and are present in the outer layer of the cell membranes of gram-negative bacteria.

The precise nature of some of the antigens together with numerous examples thereof are disclosed in U.S. Pat. No. 4,299,916 to Litman, et al., particularly at columns 16 to 23, the disclosure of which is incorporated herein by reference.

For the most part, the antigens employed in the subject invention will have a molecular weight of at least about 1,000, more usually at least about 2,500, frequently greater than 5,000. In the poly(amino acid) category, the poly(amino acids) of interest will generally be from about 5,000 to 5,000,000 molecular weight, more usually from about 20,000 to 1,000,000 molecular weight.

A wide variety of proteins may be considered: the family of proteins having similar structural features, proteins having particular biological functions, proteins related to specific microorganisms, particularly disease causing microorganisms, etc.

"Antibody"—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal). Antibodies may include a complete immunoglobulin or fragment thereof, which immunoglobulins include the various classes and isotypes, such as IgA, IgD, IgE, IgG1, IgG2a, IgG2b and IgG3, IgM, IgG1, IgG2, IgG3, IgG4 etc. Fragments thereof may include Fab, Fv and F(ab')$_2$, Fab', and the like.

"Antibody for the antigen"—an antibody that binds specifically to the antigen of the present invention.

"Binding partner for the antibody"—a compound or composition recognizing a particular spatial or polar organization of the antibody, e.g., epitopic or determinant site, or a ligand bound to the antibody. Illustrative binding partners include naturally occurring receptors, e.g., specific immunoglobulins, rheumatoid factor antibodies, lectins, protein A, complement component C1q, avidin, and the like.

"Complex"—a composite formed between the receptor for the antibody and an antibody as a result of the binding affinity of the receptor for the antibody.

"Immune complex"—a complex formed between an antigen and its cognate antibody as a result of the binding affinity of the antibody for the antigen.

"Label"—a label may be any molecule bound covalently or non-covalently to an antibody, or to another molecule. The label is a member of the signal producing system that includes a signal producing means. The label may be isotopic or nonisotopic, preferably nonisotopic. By way of example and not limitation, the label can be a catalyst such as an enzyme, a co-enzyme, a chromogen such as a fluorescer, dye or chemiluminescer, a radioactive substance, and so forth.

"Signal producing means"—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

"Signal producing system"—The signal producing system may have one or more components, at least one component being a label. The signal producing system generates a signal that relates to the presence or amount of antigen in a sample. The signal producing system includes all of the reagents required to produce a measurable signal. When the label is not conjugated to the antibody, the label is normally bound to a receptor for the antibody. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of electromagnetic radiation. For the most part, the signal producing system will involve a chromophoric substrate and enzyme, where chromophoric substrates are enzymatically converted to dyes which absorb light in the ultraviolet or visible region, phosphors, fluorescers or chemiluminescers.

The signal-producing system can include a catalyst, usually an enzyme, and a substrate and may include two or more catalysts and a plurality of substrates, and may include a combination of enzymes, where the substrate of one enzyme is the product of the other enzyme. The operation of the signal producing system is to produce a produce which provides a detectable signal related to the amount of analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

"Support"—a bibulous or non-porous water insoluble material. The support will frequently be hydrophobic or positively charged or capable of being rendered hydrophobic or positively charged, and includes particulates, bulk solids and films, matted or woven materials comprised particularly of polymers such as poly(vinyl chloride), polyethylene, polypropylene, poly(4-methylbutene), polystyrene, polymethacrylate, poly(ethylene terephthalate), nylon, poly(vinyl butyrate); glass and ceramics; and natural fibers modified to impart hydrophobic or charged properties such as alkylated or acylated cellulose, dextran, chitin and the like or surfaces coated with polylysine, protamine, dextran sulphate, polyacrylate or other ionic polymers made of any of the above materials. The support will be free of proteins that specifically bind the antibody, the antigen or the immune complex and will frequently be free of any protein or other specific binding substances.

"Ancillary Materials"—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly anionic surfactants, binding enhancers, e.g., polyalkylene glycols, or the like.

As mentioned above, the present invention involves a method for detecting an antigen in a biological sample suspected of containing the antigen. The antigen to be determined may first be solubilized by contacting the sample suspected of containing the antigen with a detergent. The sample suspected of containing an antigen can be simultaneously contacted in an aqueous medium with the detergent and the antibody for the antigen. By way of example, the sample on a collection device such as a swab may be inserted into a vial, for example, a test tube containing detergent and antibody for the antigen. Preferably, the sample can be contacted with detergent prior to being contacted with the antibody for the antigen. The sample on a swab may be inserted into a test tube containing detergent and then, with or without first reducing the concentration of the detergent, for example, by dilution, antibody for the antigen may be added.

The detergent can be anionic, cationic, nonionic, or amphoteric. Anionic detergents are preferred for purposes of the present invention and include, by way of example and not limitation, alkyl-, alkylether-, dialkyl esters-, alkylaryl-, and alpha olefin-sulfates, sulfonic acids, sulfonates, sulfosuccimates, and sulfosuccinic acids, polymerized alkyl naphthalene sulfonates, phosphate esters, free acid of complex organic phosphate esters, aliphatic hydroxylated phosphate esters, sulfated fatty acid esters, sulfated oils such an castor, sperm, soya bean, glycerol trioleate, neatsfoot, tallow, and oleic acid, n-fatty acid acyl glutamates such as n-lauroyl, n-cocoyl, n-hydrogenated tallowyl, n-mixed fatty acid acyl, carboxylated polyelectroytes, disproportionated resins, and so forth. Exemplary of cationic detergents are alkyl quaternary ammonium chlorides such as dimethyl or trimethyl alkyl or dialkyl, e.g., trimethyl soya, dimethyl dehydrogenated tallow, trimethyl cetyl, and trimethyl coco. Exemplary of nonionic detergents are Triton X 100, Tween 20, octyl glucoside, and so forth. Exemplary of amphoteric detergents are fatty acid esters of betaine and the like. Particularly preferred detergents are, for example, a deoxycholate salt, such as for example, sodium deoxycholate and sodium chenodeoxycholate, an alkylsulfate or analog thereof, alkylglucosides, CHAPS (cholamidopropyl dimethylammoniopropane sulfate), and the like. The term alkyl used above intends C8 to C20.

An unexpected advantage of employing a detergent is that detergents can be empirically selected that prevent the antibody from binding to a support in the absence of antigen whereas the antibody readily binds to the support when antigen is present. For example, chenodeoxycholate prevents antibodies to a lipopolysaccharide from *Chlamydia trachomatis* from binding to polystyrene microtiter plates unless the lipopolysaccharide is also present in the assay medium.

Temperatures employed for solubilizing the antigen are usually in the range from about 10° to 50° C., more usually from about 15° to 100° C. For the most part, relatively short times are required to solubilize an antigen. Usually, the solubilization of an antigen can take at least about 5 seconds and not more than 1 hour, more usually about 30 seconds to about 30 minutes. The time is dependent on the nature of the antigen, and the type and amount of detergent and temperature used.

The solubilization medium is generally aqueous and may contain up to 40% of an organic solvent. The pH of the solubilization medium will usually be in the range of about 2 to 12, more usually in the range of about 5 to 9. The pH is generally chosen to achieve a high level of solubilization of the antigen. Various buffers may be used to achieve and maintain the pH during the solubilization. Illustrative buffers include borate, phosphate, carbonate, Tris, barbital and the like. The particular buffer employed is not critical but one buffer may be preferred over another.

As mentioned above, the support, substantially free of specific binding proteins, is provided in combination with a medium comprising an antigen and antibody. In one embodiment, a biological sample suspected of containing the antigen and an antibody for the antigen can be combined in an aqueous medium where presumably an immune complex between the antigen and the antibody is formed. The medium can be contacted with a solid support. The medium can optionally contain a detergent as mentioned above. The sample is preferably contacted with the detergent prior to the addition of the antibody. However, alternatively, the detergent and antibody can be added to the sample simultaneously or the detergent can be added after addition of the antibody.

In another embodiment, antibody for the antigen and the support may be combined substantially simultaneously, or the antigen or antibody may be first added to the support, under conditions where binding to the support does not occur, followed by addition of the antibody or antigen, respectively. For example, the support can be contacted with an aqueous medium containing the antibody for the antigen. Subsequently, antigen can be added to the medium. Presumably, an immune complex forms in situ and binds to the support prior to the binding of the uncomplexed antibody or antigen to the support. In such a case, a detergent is preferably combined with the support prior to or substantially simultaneously with the contact between the support and the antigen and the antibody. For this purpose, the detergent may be included in one or both of the aqueous media containing the antibody or the antigen.

After formation of the combination of the support and the medium containing the antigen and antibody, the combination is incubated under conditions sufficient for the antibody when bound to the antigen to bind to the support. Usually, the incubation is carried out at a temperature of about 10° to 50° C., preferably 15° to 40° C., at a pH of about 2 to 12, preferably 5 to 9, for a period of about 5 seconds to one hour, preferably about 30 seconds to 30 minutes.

Following incubation of the combination, the presence or amount of antibody on the support or in the medium is determined as an indication of the presence of antigen in the sample. This determination can be carried out in a number of ways and examples for purposes of illustration and not limitation follow.

In one embodiment, the antibody for the antigen can be bound to a ligand, usually an organic molecule of less than 1500 molecular weight. The support can be separated from the medium, washed to remove unbound material, contacted with a labeled receptor for the organic molecule, preferably washed, and then examined for the presence of a label. The washing medium will be aqueous and may contain detergents, substances that enhance or inhibit binding such as polyethylene glycol, chaotropic salts and antichaotropic salts, buffers, e.g., phosphate buffered saline, Tris, borate, and the like. The second washing medium can contain additionally substrates or other members of a signal producing system. Suitable ligands include, for example, biotin, haptens such as, for example, fluorescein, Vitamin B12 and the like, wherein the corresponding binding partners are avidin, antibody to the hapten, and intrinsic factors, and the like, respectively. Alternatively, the ligand can be a chemically reactive group such as a maleimide or disulfide or can be a hydraize and the binding partner can have a corresponding reactive group that reacts specifically with the ligand, such as a sulfhydryl group or an aldehyde.

In another embodiment, the antibody for the antigen can be directly bound to a label, preferably an enzyme or coenzyme. After incubation, the support can be separated from the medium and will preferably then be washed. Again, the washing medium can be a buffered aqueous medium containing appropriate members of a signal producing system. In this way the presence or amount of label on the support can be determined as an indication of the presence or the analyte.

In those instances wherein the antibody for the antigen is not bound to a label, the separated support is contacted with a labeled binding partner for the antibody for the antigen, such as, for example, protein A, complement, rheumatoid factor, antibodies to the antibody for the antigen, and the like. The label, which can be attached covalently or noncovalently to the binding partner, can be any label, preferably an enzyme or coenzyme. Usually, the binding partner will be included in a separate detection medium but may be included as part of a washing solution or as part of a solution added to the support that contains all the remaining members of the signal producing system that are not bound to the support. The presence of the label on the support can then be determined as described above.

In another embodiment, the antibody for the antigen is labeled with a receptor for a ligand where the ligand can be a label such as an enzyme, fluorophore or the like, or a molecule to which is bound a label where, for example, the molecule may be a macromolecule or an organic molecule of molecular weight less than 1500. After separation of the support from the medium, the support is contacted with the ligand and the label is detected directly or where necessary, by adding the additional members of the signal producing system.

The wash solutions and the solutions containing members of the signal producing system will normally consist of aqueous buffered media at a moderate pH, generally that which provides optimum assay sensitivity. The aqueous media may be solely water or may include from 0 to 40 volume percent of a cosolvent. The pH for the medium will usually be in the range of about 4 to 11, more usually in the range of about 5 to 10, and usually will be a compromise between optimum binding of the binding members and the pH optimum for other reagents of the assay such as members of the signal producing system.

Various buffers may be used to achieve the desired pH and maintain the pH during the determination. Illustrative buffers include borate, phosphate, carbonate, tris, barbital, and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Temperatures during measurements will generally range from about 10° to 50°, more usually from about 15° to 40° C.

The concentration of antigen which may be assayed will generally vary from about $10^{-4}$ to $10^{-15}$M, more usually from about $10^{-6}$ to $10^{-14}$M. Considerations, such as the amount of non-specific binding of label to the support, the particular detection technique and the concentration of the antigen of interest will normally determine the concentrations of the various reagents.

While the concentrations of the various reagents in the assay medium will generally be determined by the concentration of the antigen, the final concentration of each of the reagents will normally be determined empirically to optimize the sensitivity of the assay.

After all of the reagents have been combined either simultaneously or sequentially and any complex that has been formed has bound to the support, the signal produced by the signal producing system with a sample of interest may be compared with the signal produced with a sample that is known to be free of the antigen in order to establish the presence of the antigen in the sample tested. A significantly higher signal produced with the test sample signifies the presence of the antigen.

The use of the method of the invention maintains or increases the sensitivity and/or specificity of the assays while decreasing the amount of antibody for the antigen needed to form a complex with antigen in a sample tested. By forming the complex in solution about 100 fold less antibody is utilized than when the reaction is carried out on a solid phase. In a typical sandwich assay for an antigen, antibody bound to a support is incubated and forms a complex with the antigen. In the method of the present invention the immune complex comprising antigen and antibody for the antigen is performed or formed in situ in solution and then binds to a support that has no specific binding protein on its surface. The immune complex is detected by production of a signal that is related to the presence of antigen in the sample. The signal is produced by virtue of the presence in the complex of a label. Either the antibody contains a label or is capable of combining with a label such as by binding to a binding partner for the antibody. By choice of the label, antibody and support and conditions employed in performing the assay a detectable signal is observable in the medium and/or on the support.

In a particular embodiment of the invention for the detection of Chlamydia, a buffer containing antibody for Chlamydia and the detergent chenodeoxycholate (CDOC) is added to a well in a polystyrene microtiter plate. The sample suspected of containing Chlamydia is contacted with CDOC, and transferred to the same well. The mixture is incubated for about 90 minutes at about 37° C. and then washed, preferably with a phosphate buffer solution. Thereafter, the plate is contacted with a labeled binding partner for the antibody for Chlamydia. A preferred binding partner is antiglobulin labeled with an enzyme, preferably a peroxidase such as horse radish peroxidase. After incubation at about 37° C. for sixty minutes, the support is washed and a solution of the substrates, hydrogen peroxide and tetramethylbenzidine (TMB) and hydrogen peroxide are added. After incubation at about 37° C. for about 30 minutes, optionally the reaction can be stopped by addition of sulfuric acid. Thereafter, the absorption of the substrate solution at 450 nm is read and compared to the absorption produced in a similar manner with a sample known to be free of Chlamydia antigen.

As a result of binding the immune complex to the support, a simplified protocol can be employed and a strong detectable signal is obtained for accurate determination of antigen in a sample. By performing the complex or forming the complex in situ, the amount of antibody used in the assay is reduced without sacrificing the sensitivity of the assay. Furthermore, the invention offers an advantage over the methodology of the prior art in that the number of washing and separation steps is reduced.

EXAMPLES

The invention is demonstrated further by the following illustrative examples.

Before proceeding with a description of the examples, the following terms are defined:
cfu—colony forming units
CDOC—chenodeoxycholate
HRP—horseradish peroxidase
PBS—(phosphate buffered saline) 0.01M $NaH_2PO_4$, 0.15M NaCl, 0.02% $NaN_3$
BSA—Bovine serum albumin
ABTS—2,2'-azinobis(3-ethylbenzthiazolinesulfonic acid)
TMB—tetramethylbenzidine
DTT—dithiothreitol
Solubilization Buffer (SDB)—0.05% CDOC, 5 mM DTT, DPBS (pH 7.2)
IgG—Immunoglobulin G IgG₃—IgG3 is isotype of IgG FBS—50% fetal calf serum in 0.01M Tris, pH 7.5 and 0.2% Tween 20

DPBS—Dulbeccos phosphate buffered saline

RαmIgG3—rabbit anti-mouse IgG3 antibodies

FBS—fetal bovine serum

1H11—mouse monoclonal antibody (IgG$_3$) which is specific for lipopolysaccharide of chlamydia antigen; see Stephens, R. S.; Tam, M. R.; Kuo, C-C; Nowinski, R. C. "Monoclonal antibodies to *Chlamydia trachomatis*: Antibodies specificities and antigen characterization." *J Immunol,* 128: 1083–1089 (1982).

Rabbit anti-chlamydia antisera—rabbit polyclonal antisera raised specifically against chlamydia antigen (solubilized and whole).

Conjugates—horseradish peroxidase (HRP) labeled affinity purified antibody to rabbit IgG (H and L chain) goat (goat anti-rabbit IgG) and HRP labeled affinity purified antibody to mouse IgG (H and L chain) goat (goat anti-mouse IgG), were purchased from Kirkeggard and Perry Laboratories (Maryland).

EXAMPLE 1

A sample suspected of containing chlamydia was collected on a swab and the swab and 1.0 ml of 0.10% CDOC were combined for about 15 minutes. The swab was discarded and the 100 μl of mixture was transferred to a plate, mixed with 100 μl of 0.1% CDOC containing 0.1 μg anti-chlamyia antibody, and incubated at 37° C. After ninety minutes, the plate was washed with PBS. Goat anti-rabbit-HRP (3 pmols) in PBS with 50% FBS was added. After incubation for sixty minutes at 37° C., the support was washed with PBS containing Tween-20. Thereafter, 0.10 ml TMB substrate (0.8 mmol/l) was added. The support was incubated at 37° C. for 30 minutes. The reaction was stopped with 0.1 ml H$_2$SO$_4$ (1N) and the reaction was read at 450 nm. The results are summarized in Table 1.

TABLE I

| Patient Sample | OD$_{450}$ With anti-chlamydia Antibody | Without anti-chlamydia Antibody (conjugate control) |
|---|---|---|
| 1 (containing chlamydia antigen) | 1.250 | 0.067 |
| 2 (negative for chlamydia antigen) | 0.084 | 0.081 |

EXAMPLE 2

(A) 100 μl of Solubilization Buffer (SDB) or PBS was added to a support. 10 μl of stock chlamydia elementary bodies (Lot RR02) and 10 μl of 1H11, monoclonal anti-chlamydia LPS (100 μg/ml) in 20 mg/ml BSA in PBS was added to the support. After incubation for 1 hour at 37° C., the mixture was washed twice in PBS. RαmIgG3-HRP (1:1000) in PBS with 20 mg/ml BSA was added to the support. After incubation at 37° C. for 1 hour, 0.1 ml ABTS (2 mmol/l) was added. The reaction was read at 414 nm. The results are summarized in Table 2.

(B) For purposes of comparison, a traditional ELISA sandwich type assay not within the scope of the present invention was conducted.

100 μl of Solubilization Buffer (SDB) or PBS was added to a support. 10 μl of stock chlamydia elementary bodies (Lot RR02) (1:500) was then added to the support. After incubating for one hour at 37° C. the support was washed twice in PBS. 10 μl monoclonal anti-chlamydia antibody, 1H11 (100 μg/ml) with 20 mg/ml BSA was added to the plate. After incubation at 37° C. for one hour, the plate was washed with PBS. RαmIgG3-HRP (1:1000) in PBS with 20 mg/ml BSA was added to the support. After incubation at 37° C. for one hour 0.1 ml ABTS (2 mmol/l) was added. The reaction was read at 414 nm. The results are summarized in Table 2.

TABLE 2

| ABSORBANCE at 414 nM | | | |
|---|---|---|---|
| | No Chlamydia Antigen Present | Chlamydia Antigen 1:5000 in PBS | Chlamydia Antigen 1:5000 in SDB |
| A | 0.34 | 0.46 | 2.50 |
| B | 0.15 | 0.18 | 0.17 |

| Assay Controls | | A | B |
|---|---|---|---|
| Conjugate Background (PBS) | (Antigen in PBS; No Antibody; Conjugate Present) | 0.17 | 0.15 |
| Conjugate Background (SDB) | (Antigen in SDB; No Antibody; Conjugate Present) | 0.17 | 0.14 |
| Substrate Background | (No Antigen; No Antibody; No Conjugate) | 0.13 | 0.12 |

EXAMPLE 3

A sample suspected of containing chlamydia was collected on a swab and was incubated in 1 ml of a modified sodium tetradecyl sulfate (0.1% in 0.1M acetate buffer pH 4.5, 6 mM DTT, 5 mM EDTA, and 50 mM glucose) for 15 minutes at room temperature. After mixing, the swab was removed and discarded and 50 μl of the solution was incubated for 5 minutes at room temperature with 50 μl of a solution containing 20 ng/ml of rabbit antibodies to chlamydia, 0.2M Tris buffer pH 7.5, 0.01% BSA, and glucose oxidase immobilized on latex beads. Thereafter the solution was added to an inlet port in a sheet covering a strip of glass fiber paper. After the solution had been absorbed, 50 μl of FBS was added and allowed to soak into the strip followed by addition of 50 μl of horseradish peroxidase-goat anti rabbit Ig in FBS. After 5 minutes, another 50 μl portion of FBS was added followed by addition of 1000 μl of citrate buffer (0.1M pH 5.5), and 50 μl of a solution containing a chromogenic peroxidase substrate, 0.05M glucose, and 0.1M citrate, pH 5.5, where each solution was allowed to soak into the strip before addition of the next solution. After incubation for 5 minutes at room temperature, the color formed on the strip at the inlet port was compared to the color formed in a like experiment using a sample that was known to be free of chamydial antigen and the results were read. The results are summarized in Table 3.

TABLE 3

| Chlamydia antigen | Color intensity* |
|---|---|
| present | 500 |
| not preset | 45 |

*Arbitrary scale

EXAMPLE 4

Five endocervical swab samples known to be negative for *Neisseria gonorrhoeae* were collected on swabs and the samples were extracted using 1 ml 0.1% CDOC, 0.1% Thimerosal, DPBS-pH 7.2. The extracts were pooled. A portion of the sample pool was taken and supplemented with a known amount of *N. gonorrhoeae*. Rabbit polyclonal antibody was diluted in 0.1% CDOC 0.01% Thimerosal DPBS-pH 7.2 and 100 μl of the antibody solution added to each well of a microtiter plate. Immediately thereafter 100 μl of the extracted (negative or supplemented) sample was added to each well. After incubation for ninety minutes at 37° C., the mixture was removed and the well was washed in 0.1% Tween in DPBS. Thereafter, 100 μl of goat anti-rabbit IgG-HRP conjugate appropriately diluted in 50% DPBS/50% FBS was added to each well. After incubation for about sixty minutes at 37° C., the mixture was removed and the well was washed with 0.1% Tween in DPBS and then 100 μl of TMB solution was added to each well. After incubation at room temperature for thirty minutes 100 μl of 1N $H_2SO_4$ was added to each well and the reaction was read at 450 nm. The experiment was repeated with a second antibody lot and new set of patient sample extract. The results are summarized in Table 4.

TABLE 4

| N. gonorrhoea | A 450 (n = 2) | |
|---|---|---|
| cfu/well | Ab (Lot #1) | Ab (Lot #2) |
| 0 | 0.130 | 0.137 |
| 50 | 0.215 | 0.394 |
| 500 | 0.894 | 1.560 |
| 5000 | >2.0 | >2.0 |

EXAMPLE 5

A sample suspected of containing *N. gonorrhoeae* was collected on a swab and was incubated in 1 ml of a modified sodium tetradecyl sulfate (0.2% in 0.1M acetate buffer pH 4.5, mM DTT, 5 mM EDTA) for 15 minutes at room temperature. After mixing, the swab was removed and discarded and 50 μl of the solution was incubated for 10 min at room temperature with 50 μl of a solution containing 40 ng/μl of rabbit antibodies to *N. gonorrhoeae*, 2% $H_2O_2$, 0.2M Tris buffer pH 7.5, and glucose oxidase immobilized on latex beads. Thereafter the solution was added to an inlet port in a sheet covering a strip of glass fiber paper.

After the solution had been absorbed, 50 μl of FBS was added and allowed to soak into the strip followed by addition of 50 μl of horseradish peroxidase-goat anti rabbit Ig in FBS. After 5 minutes, another 50 μl portion of FBS was added followed by addition of 1000 μl of citrate buffer (0.1M pH 5.5), and 50 μl of a solution containing a chromogenic peroxidase substrate, 0.05M glucose, and 0.1M citrate, pH 5.5, where each solution was allowed to soak into the strip before addition of the next solution. After incubation for 5 minutes at room temperature the color formed on the strip at the inlet port was compared to the color formed in a like experiment using a sample that was known to be free of *N. gonorrhoeae* antigen and the results were read. The results are summarized in Table 5.

TABLE 5

| N. Gonorrhoeae Antigen | Color Intensity* |
|---|---|
| Present | 600 |
| Not present | 30 |

*Arbitrary scale

The above examples demonstrate that accurate and sensitive assays for Chlamydia and *N. gonorrhoeae* can be carried out in accordance with the above described invention.

Although the foregoing invention has been described in some detail by way of illustration and example for purposes of clarity of understanding, it will be understood that certain changes and modifications can be practiced within the scope of the invention.

What is claimed is:

1. A method for detecting an antigen in a biological sample suspected of containing an antigen, said method comprising
    a. providing in combination a solid support, which is hydrophobic or positively charged and substantially free of proteins, binding partners specific for said antigen, binding partners specific for antibody specific for said antigens, and non-ionic binders for an immune complex of said antigen and said antibody, and an aqueous medium comprising an antigen from said sample and an antibody specific for said antigen;
    b. incubating said combination under conditions sufficient for said antibody when bound to said antigen to bind to said support; and
    c. determining the antibody bound to said support or in said medium, the presence or amount thereof being related to the presence of antigen in said sample.

2. The method of claim 1 wherein said support is separated from said medium prior to step c.

3. The method of claim 1 wherein said antigen is from a gram-negative bacterium.

4. The method of claim 1 wherein said sample is contacted with a detergent to solubilize said antigen prior to or during step a.

5. The method of claim 1 wherein said support is bibulous.

6. The method of claim 2 wherein said separated support is washed prior to step c.

7. The method of claim 1 wherein said antibody specific for said antigen has a label bound to it or said medium includes a labeled binding partner specific for said antibody.

8. The method of claim 7 wherein said label is selected from the group consisting of enzymes, coenzymes, fluorescers, chemiluminescers, and radioactive substances.

9. The method of claim 7 wherein said binding partner specific for said antibody specific for said antigen is selected from the group consisting of antiglobulin, protein A and complement.

10. The method of claim 1 wherein said support is contacted with a detection medium comprising a labeled binding partner specific for said antibody specific for said antigen and said determining comprises examining said support for the presence of a label.

11. The method of claim 10 which further includes the step of separating said support from said detection medium prior to said determining.

12. The method of claim 7 wherein said antibody specific for said antigen is conjugated to an organic molecule of molecular weight less than 1500 and said medium includes a label bound to a receptor specific for said organic molecule and said determining comprises examining said support for the presence of said label.

13. A method for detecting an antigen of gram-negative bacteria in a biological sample suspected of containing said bacteria, said method comprising
   a. providing in combination a plastic solid support, which is hydrophobic or positively charged and is substantially free of proteins, binding partners specific for said antigen, binding partners specific for antibody specific for said antigen, and non-ionic binders for an immune complex of said antigen and said antibody, and an aqueous medium comprising a mixture of an antigen of said bacteria and an antibody specific for said antigen;
   b. incubating said combination under conditions sufficient to said antibody when bound to said antigen to bind to said support;
   c. separating said support from said medium; and
   d. determining the antibody on said support, the presence or amount thereof being related to the presence of said gram-negative bacteria in said sample.

14. The method of claim 13 wherein said sample is contacted with a detergent to solubilize said antigen prior to or during step a.

15. The method of claim 13 wherein said antibody specific for said antigen is bound to a label.

16. The method of claim 13 wherein prior to step d said antibody is contacted with a labeled binding partner for said antibody.

17. The method of claim 15 wherein said label is selected from the group consisting of enzymes, coenzymes, fluorescers, chemiluminescers, and radioactive substances.

18. The method of claim 16 wherein said receptor specific for said antibody is selected from the group consisting of antiglobulin, protein A and complement.

19. The method of claim 13 wherein said separated support is contacted with a detection medium comprising a label bound to a receptor specific for said antibody and said determining comprises examining said support for the presence of said label.

20. The method of claim 19 which further includes the step of separating said support from said detection medium prior to said determining.

21. The method of claim 13 wherein said antibody is conjugated to an organic molecule of molecular weight less than 1500 and said medium includes a label bound to a receptor specific for said organic molecule and said determining comprises examining said support or said medium for the presence of said label.

22. A method for detecting an antigen of a gram-negative bacteria in a biological sample comprising:
   a. providing in combination a solid support, which is hydrophobic or positively charged and is substantially free from proteins, binding partners specific for said antigen, binding partners specific for antibody specific for said antigen, and non-ionic binders for an immune complex of said antigen and said antibody, and an aqueous medium containing a biological sample suspected of containing an antigen from said gram-negative bacteria and an antibody specific for said antigen;
   b. incubating said combination under conditions sufficient for said antibody when bound to said antigen to bind to said support; and
   c. determining said antibody on said support, the presence or amount thereof being related to the presence of said bacteria in said sample.

23. The method of claim 22 wherein said support is separated from said medium prior to step c.

24. The method of claim 22 wherein said gram-negative bacteria is selected from the group consisting of *Chlamydia trachomatis, Chlamydia psittaci,* and *Neisseria gonorrhoeae.*

25. The method of claim 22 wherein said sample is contacted with a detergent to solubilize antigens in said bacteria prior to step a.

26. The method of claim 25 wherein said detergent is selected from the group consisting of a deoxycholate salt, an alkylsulfate, an alkylglucoside and CHAPS.

27. The method of claim 23 wherein said separated support is washed prior to step c.

28. The method of claim 22 wherein said antibody for said antigen has a label bound to it or said medium includes a labeled binding partner for said antibody.

29. The method of claim 28 wherein said label is selected from the group consisting of enzymes, coenzymes, fluorescers, chemiluminescers, and radioactive substances.

30. The method of claim 28 wherein said binding partner for said antibody is selected from the group consisting of antiglobulin, protein A and complement.

31. The method of claim 30 wherein said support is contacted with a detection medium comprising said labeled binding partner for said antibody and said determining comprises examining said support for the presence of said label.

32. The method of claim 31 wherein said label is selected from the group consisting of enzymes, coenzymes, fluorescers, chemiluminescers, and radioactive substances.

33. The method of claim 31 which further includes the step of separating said support from said detection medium prior to said determining.

34. The method of claim 28 wherein said antibody is conjugated to an organic molecule of molecular weight less than 1500 and said medium includes a label bound to a receptor for said organic molecule and said determining comprises examining said support for the presence of said label.

35. The method of claim 34 wherein said label is selected from the group consisting of enzymes, coenzymes, fluorescers, chemiluminescers, and radioactive substances.

36. The method of claim 34 wherein said receptor for said organic molecule is selected from the group consisting of antibody and avidin.

37. A method for detecting an integer of a gram-negative bacteria in a biological sample comprising:
   a. contacting a bibulous, solid support, which is hydrophobic or positively charged and is substantially free of proteins, binding partners specific for said antigen, binding partners specific for antibody specific for said antigen, and non-ionic binders for an immune complex of said antigen and said antibody, with an immune complex comprising an antigen associated with said bacteria from said sample and an antibody for said antigen wherein said complex is preformed;

b. incubating said support with said complex for a time sufficient for said complex to bind to said support; and c. determining said antibody on said support, the presence of amount thereof being related to the presence of said bacteria in said sample.

38. The method of claim 37 wherein said gram-negative bacteria is selected from the group consisting of *Chlamydia trachomatis, Chlamydia psittaci,* and *Neisseria gonorrhoeae.*

39. The method of claim 37 wherein said sample is contacted with a detergent to solubilize antigens in said bacteria prior to or during step a.

40. The method of claim 39 wherein said detergent is selected from the group consisting of a deoxycholate salt, an alkylsulfate, an alkylglucoside and CHAPS.

41. The method of claim 37 wherein said antibody has a label bound to it or said medium includes a labeled binding partner for said antibody.

42. The method of claim 41 wherein said label is selected from the group consisting of enzymes, coenzymes, fluorescers, chemiluminescers, and radioactive substances.

43. The method of claim 41 wherein said binding partner for said antibody is selected from the group consisting of antiglobulin, protein A and complement.

44. The method of claim 41 wherein said support is separated from said medium and is contacted with a detection medium comprising said labeled binding partner for said antibody and said determining comprises examining said support for the presence of a label.

45. The method of claim 44 wherein said label is selected from the group consisting of enzymes, coenzymes, fluorescers, chemiluminescers, and radioactive substances.

46. The method of claim 44 wherein said binding partner for said antibody is selected from the group consisting of antiglobulin, protein A and complement.

47. The method of claim 41 wherein said antibody is conjugated to an organic molecule of molecular weight less than 1500 and said medium includes a labeled receptor for said organic molecule and said determining comprises examining said support for the presence of a label.

48. The method of claim 47 wherein said label is selected from the group consisting of enzymes, coenzymes, fluorescers, chemiluminescers, and radioactive substances.

49. The method of claim 48 wherein said receptor for said organic molecule is selected from the group consisting of antibody and avidin.

50. A method for detecting an antigen associated with *Chlamydia trachomatis* in a biological sample suspected of containing *Chlamydia trachomatis,* said method comprising:

a. providing in combination a solid support, which is hydrophobic or positively charged and is substantially free of proteins, binding partners specific for said antigen, binding partners specific for antibody specific for said antigen, and non-ionic binders for an immune complex of said antigen and said antibody, and an aqueous medium containing a biological sample suspected of containing *Chlamydia trachomatis* and an antibody for said antigen;

b. incubating said combination under conditions sufficient for said antibody when bound to said antigen to bind to said support; and c. determining the amount of said antibody on said support as a measure of said antigen in said sample.

51. The method of claim 50 wherein said sample is contacted with a detergent to solubilize said antigen prior to or during step a.

52. The method of claim 51 wherein said detergent is selected from the group consisting of a deoxycholate salt, an alkylsulfate, an alkylglucoside and CHAPS.

53. The method of claim 50 wherein said support is plastic.

54. The method of claim 50 wherein said support is washed after separating from said medium.

55. The method of claim 50 wherein said antibody has a label bound to it or said medium includes a labeled binding partner for said antibody.

56. The method of claim 55 wherein said label is selected from the group consisting of enzymes, coenzymes, fluorescers, chemiluminescers, and radioactive substances.

57. The method of claim 55 wherein said binding partner is selected from the group consisting of antiglobulin, protein A and complement.

58. The method of claim 50 wherein said support is separated from said medium and is contacted with a detection medium comprising a label bound to a binding partner for said antibody and said determining comprises examining said support for the presence of said label.

59. The method of claim 58 wherein said label is selected from the group consisting of enzymes, coenzymes, fluorescers, chemiluminescers, and radioactive substances.

60. The method of claim 58 wherein said binding partner is selected from the group consisting of antiglobulin, protein A and complement.

61. The method of claim 58 which further includes the step of separating said support from said detection medium prior to said determining.

62. The method of claim 50 wherein said antibody is conjugated to an organic molecule of molecular weight less than 1500 and said medium includes a label bound to a receptor for said organic molecule and said determining comprises examining said support for the presence of said label.

63. The method of claim 62 wherein said label is selected from the group consisting of enzymes, coenzymes, fluorescers, chemiluminescers, and radioactive substances.

64. The method of claim 62 wherein said receptor for said organic molecule is selected from the group consisting of antibody and avidin.

65. A method for detecting an antigen associated with *Neisseria gonorrhoeae* in a biological sample suspected of containing *Neisseria gonorrhoeae,* said method comprising a. providing in combination a solid support, which is hydrophobic or positively charged and is substantially free of proteins, binding partners specific for said antigen, binding partners specific for antibody specific for said antigen, and non-ionic binders for an immune complex of said antigen and said antibody, and an aqueous medium containing a biological sample suspected of containing *N. gonorrhoeae* and an antibody for said antigen;

b. incubating said combination under conditions sufficient for said antibody when bound to said antigen to bind to said support; and c. determining the amount of said antibody on said support as a measure of said antigen in said sample.

66. The method of claim 65 wherein said sample is contacted with a detergent to solubilize said antigen prior to or during step a.

67. The method of claim 66 wherein said detergent is selected from the group consisting of a deoxycholate salt, an alkylsulfate, an alkylglucoside and CHAPS.

68. The method of claim 65 wherein said support is plastic.

69. The method of claim 65 wherein said support is washed after separating from said medium.

70. The method of claim 65 wherein said antibody has a label bound to it or said medium includes a labeled binding partner for said antibody.

71. The method of claim 70 wherein said label is selected from the group consisting of enzymes, coenzymes, fluorescers, chemiluminescers, and radioactive substances.

72. The method of claim 70 wherein said binding partner is selected from the group consisting of antiglobulin, protein A and complement.

73. The method of claim 65 wherein said support is separated from said medium and is contacted with a detection medium comprising a label bound to a binding partner for said antibody and said determining comprises examining said support for the presence of said label.

74. The method of claim 73 wherein said label is selected from the group consisting of enzymes, coenzymes, fluorescers, chemiluminescers, and radioactive substances.

75. The method of claim 73 wherein said binding partner is selected from the group consisting of antiglobulin, protein A and complement.

76. The method of claim 73 which further includes the step of separating said support from said detection medium prior to said determining.

77. The method of claim 65 wherein said antibody is conjugated to an organic molecule of molecular weight less than 1500 and said medium includes a label bound to a receptor for said organic molecule and said determining comprises examining said support for the presence of said label.

78. The method of claim 77 wherein said label is selected from the group consisting of enzymes, coenzymes, fluorescers, chemiluminescers, and radioactive substances.

79. The method of claim 77 wherein said receptor for said organic molecule is selected from the group consisting of antibody and avidin.

* * * * *